United States Patent [19]

Stevens et al.

[11] 4,310,935
[45] Jan. 19, 1982

[54] FOOTREST FOR AN X-RAY TABLE

[75] Inventors: Edward P. Stevens, Broomfield; Jack H. Zabel, Milwaukee, both of Wis.

[73] Assignee: General Electric Company, Schenectady, N.Y.

[21] Appl. No.: 147,777

[22] Filed: May 8, 1980

[51] Int. Cl.³ .................... A47C 20/02; A61G 7/06
[52] U.S. Cl. ............................................. 5/80; 5/430
[58] Field of Search ............... 5/80, 67, 73, 430, 425, 5/443, 444; 250/456, 439 R

[56] References Cited

U.S. PATENT DOCUMENTS

| 2,735,738 | 2/1956 | Berne | 5/444 X |
| 2,816,296 | 12/1957 | Wilson | 5/444 |
| 3,521,876 | 7/1970 | Smith | 250/456 X |
| 3,581,088 | 5/1971 | Engels | 250/456 |
| 3,818,516 | 6/1974 | Hopper et al. | 5/67 |
| 3,866,251 | 2/1975 | Pounds | 5/444 |
| 3,997,792 | 12/1976 | Conrad et al. | 5/425 X |

Primary Examiner—Stephen J. Novosad
Attorney, Agent, or Firm—Ralph G. Hohenfeldt

[57] ABSTRACT

An x-ray table footrest assembly comprises a support base for extending across the table top. A platform rotationally mounted to the base. A pair of spring biased latches mounted to the base for engaging side rails on the table top. Sliding bars which move linearly in response to platform rotation are interfered with by the latches unless the latches are securely engaged with the side rails.

3 Claims, 5 Drawing Figures

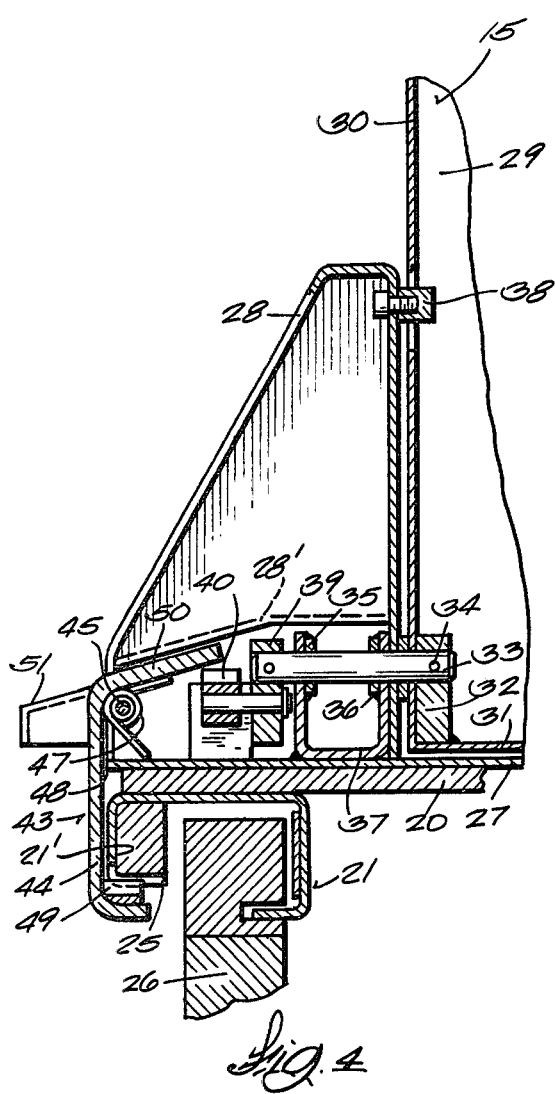
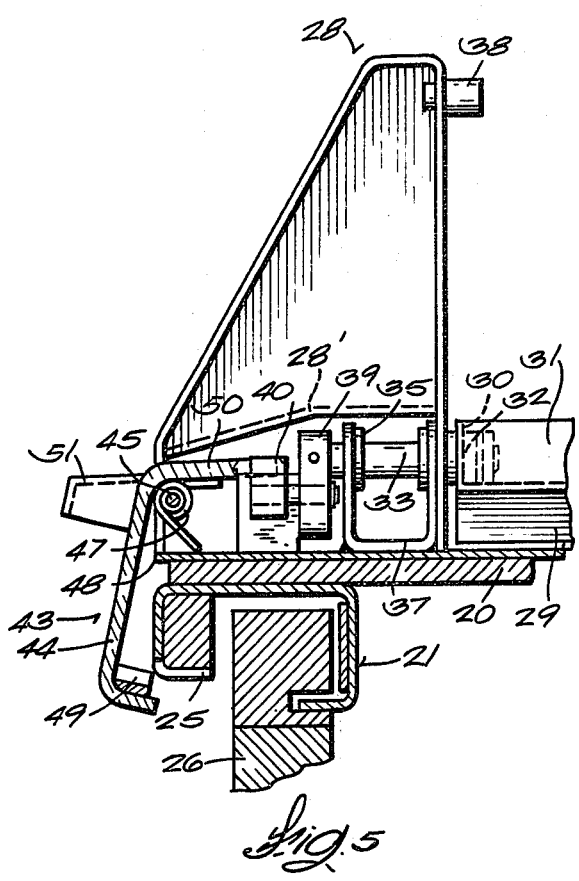

FOOTREST FOR AN X-RAY TABLE

This invention relates to a footrest assembly for supporting a patient on the top of a tiltable x-ray table.

A footrest assembly is installed on an x-ray table top when the diagnostic procedure requires the patient to be established in an upright position. A wide variety of footrest assemblies have been produced. Most, if not all of them are provided with some means for engaging them with notches in rails at the laterally spaced apart sides of the x-ray table top for preventing slippage of the footrest when the x-ray table is tilted upright and the patient's weight is applied. In prior art footrest designs, it is possible for the latches to be improperly set without the x-ray technician being aware of it so the footrest may slip when a load is applied and possibly cause injury and trauma to a patient. Heretofore, footrests have not been provided with any means for indicating an unsafe condition nor for preventing use until the footrest assembly is securely latched onto the x-ray table top.

SUMMARY OF THE INVENTION

The new footrest assembly described herein overcomes the above-indicated disadvantages in that it provides a clear indication to the user as to whether it is securely latched to the x-ray table top. In addition, means are provided for preventing the footrest platform from being swung from the inactive position, in which it is disposed when the assembly is first installed on the table, to the active position in which it is disposed for having the patient's feet rest on it.

Briefly stated, the new footrest assembly comprises a rigid support or base which extends laterally across the x-ray table top. Latches are provided at opposite ends of the support for engaging it in a selected one of a series of position holding means such as slots in rails which run along the sides of the table top. The footrest platform is mounted to the support on coaxial pintle shafts for swinging from an inactive position, wherein the platform is nominally parallel to the x-ray table top, to an active position wherein the platform is nominally perpendicular to the table top. Movable stop members are driven by rotation of the pintles. If the latches are not properly engaged to the side rails, they interfere with movement of the stop members and thereby prevent swinging of the platform to active position. When the latches are properly set, they are removed from interfering relationship with respect to the stop members and the platform can be swung to active position.

How the foregoing and other more specific objects of the invention are achieved will be evident in the more detailed description of a preferred embodiment of the invention which will now be set forth in reference to the drawings.

DESCRIPTION OF THE DRAWINGS

FIG. 4 is a fragmentary section taken on the irregular line corresponding with 4—4 in FIG. 2, the latch in this view being properly set for enabling the footrest platform to be swung or rotated to its active position; and FIG. 5 is similar to FIG. 4 except that the latch is shown as being improperly set so as to interfere with rotation of the platform and cause it to remain in a folded condition or the inactive position in which it is shown in FIG. 5.

DESCRIPTION OF A PREFERRED EMBODIMENT

Figure 1:
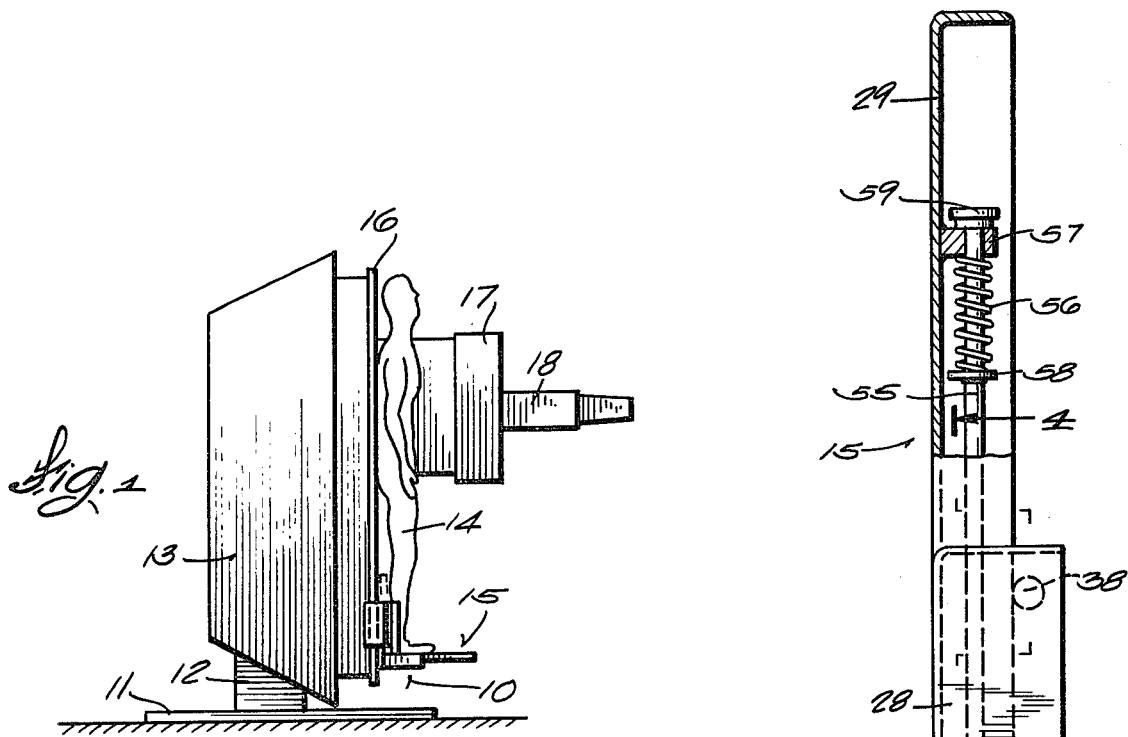
FIG. 1 is a front elevation view of a typical x-ray table on which the new footrest assembly is installed.

FIG. 1 shows a typical x-ray table on which the new footrest assembly 10 is installed. The table comprises a base 11 and a column 12 on which an x-ray table body 13 is mounted for tilting in at least one direction between horizontal and vertical attitudes. The table in FIG. 1 is shown tilted to a vertical attitude wherein a patient 14 is supported in an upright position with the feet of the patient resting on footrest platform 15. The back of the patient is resting against the x-ray transmissive table top which is generally designated by the reference numeral 16. In this particular table, the x-ray tube, not shown, is mounted within table body 13 for projecting an x-ray beam through table top 16 and patient 14. The x-ray image is formed in a combination spot film device 17 or, alternatively, in an image intensifier system 18, said device and system being shown diagrammatically since they are conventional.

Figure 2:
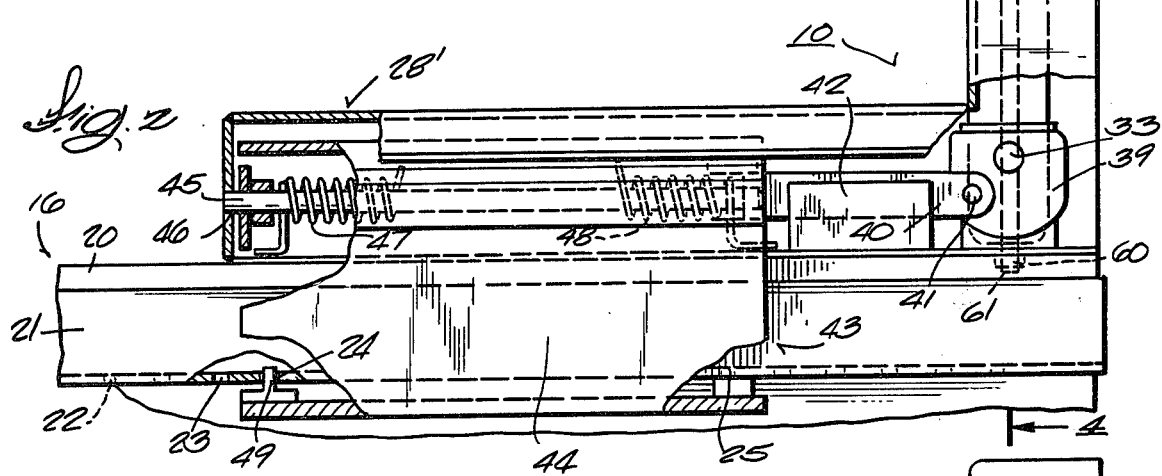
FIG. 2 is an enlarged side view of the footrest assembly installed on an x-ray table top which is shown partially, the platform of the assembly being in its active position, or generally perpendicular to the plane of the table top.

As can be seen in FIG. 2, the x-ray table top assembly 16 comprises a planar sheet or panel 20 of x-ray transmissive material which is supported on channel-shaped side rails such as the one marked 21 in FIG. 2. These side rails are coextensive with the length or longitudinal dimension of the table top and there is one on each side of the table top. The cross sectional configuration of a typical side rail 21 may be seen in FIG. 4. The rails have inwardly turned edges in which there are a series of spaced apart footrest position holding means which in this example are constituted by notches typified by those marked 22–25 in FIG. 2. There are corresponding holding means or notches in the opposite table top side rail which is not shown. Closely spaced apart protuberances, not shown, could be used in place of the notches or slots. The table top is supported and fastened on suitable structural members 26 extending from within the table body or housing 13.

As shown in FIG. 4, the platform assembly comprises a support plate 27 which is adapted for sliding over and resting on x-ray transmissive table top sheet 20. A pair of arms, actually hollow housing members such as the one marked 28 are joined in perpendicularity with support plate 27 and form part of the support or base of the footrest assembly 10.

The footrest platform 15 comprises a planar metal panel 29 which has its edges down to form stiffening flanges such as those marked 30 and 31 which are joined together to form a rigid rectangular frame. Platform surface 29 is ordinarily covered with a rubber or plastic anti-slip tread, not shown. Metal blocks such as the one marked 32 are anchored, such as by welding, in two corners of the platform. A shaft or pintle 33 is fixed in block 32 with a pin 34 or any other suitable means. There is, of course, a pintle shaft similar to pintle 33 extending laterally from the opposite edge of the footrest platform and this pintle is coaxial with pintle 33. Since the structures are similar on both sides of the platform, it is only necessary to describe one, such as the one depicted in FIGS. 4 and 5.

Pintle 33 extends through a pair of bushings 35 and 36 that are mounted in a bracket 37 which has a U-shaped cross section as can be seen in FIGS. 4 and 5. As shown in FIG. 4, platform assembly 15 is in parallelism with arm 28 or perpendicular to the plane of table top 20 which is the active or use position of the footrest platform. This is designated as the active position of the footrest since it is in a position and at an angular attitude wherein the patient's feet may rest on it. It corresponds with the position in which platform 15 is disposed in FIG. 2. When the platform has been rotated to this position, it is precluded from rotating beyond perpendicularity with table top 20 by stop pins 38 which extend laterally inwardly from rigid arms 28.

As can be seen particularly well in FIGS. 4 and 2, the outboard end of pintle shaft 33 has a link 39 fixed to it. As can be seen in FIG. 2, link 39 has a stop member in the form of a sliding bar 40 coupled to it with a pivot pin 41. Because of the axis of pivot pin 41 being offset from the axis of pintle shaft 33, rotation of platform 15 on the pintle shaft will result in linear translation of stop member 40. The stop member is supported in an internally slotted guide element 42 which assures that the stop member or bar member 40 will travel linearly. Upstanding arm 28 has a hollow extension member 28' joined with it. Member 28' is disposed in substantial parallelism with the table top panel 20 when the footrest assembly is installed.

Manually operable latch members such as the one marked 43 are mounted within hollow extensions 28'. These latch members are like bell cranks which have two arms 44 and 50. Typical latch member 43 is supported for pivoting on a pin 45 which extends longitudinally of the table top and has its ends suitably fixed in arm extension 28' as indicated at 46 in FIG. 2. A pair of torsion springs 47 and 48 surround shaft 45. These torsion springs are preloaded so they have a tendency to urge latch member 43 into counterclockwise rotation as viewed in FIG. 4 where the latch member is at the limit of its counterclockwise rotation by reason of it having struck the stopping edge 48 on the support 47. Latch member 43 is comprised of first and second integral and differently angulated arm elements 44 and 50, the first of which has a pawl 49 for releasably engaging or registering in any selected holding means such as a slot or notch 25 in the table side rail 21. When pawl 49 is registered in notch 25 in FIG. 4, latch member 43 is able to attain its maximum counterclockwise rotation. When any of the pawls 49 are misaligned and not registered in a holding slot or notch 25 as is the case in FIG. 5, it will be seen that the pawl will strike an imperforate wall 21' of the rail 21 such that another arm element 50 of the latch will be rocked to a horizontal attitude as in FIG. 5 as compared with its upwardly inclined attitude in FIG. 4.

Figure 3:
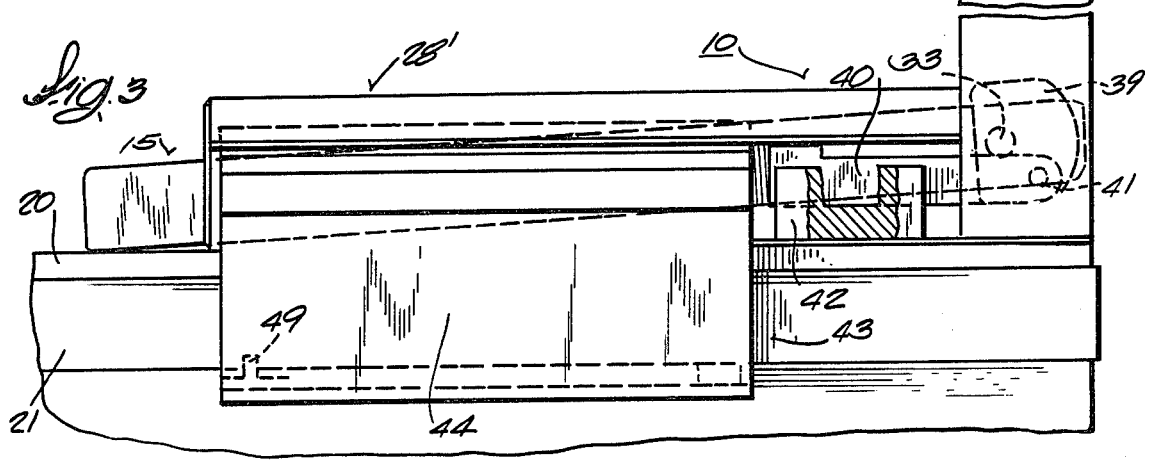
FIG. 3 is a side view of the footrest platform when disposed in its inactive position.

When the pawls 49 on each latch member are not properly registered in the holding slots 25 as in FIG. 5, the second arm portion element 50 of latch member 43 is placed in a position where it interferes with translation of the sliding bar stop member 40 which, as explained earlier, is subject to translation when platform 15 is rotated toward perpendicularity with the table top panel 20. Thus, when latch 43 is disposed as in FIG. 5, platform 15 cannot be rotated out of inactive position. Instead, the platform 15 remains locked in the position in which it is shown in FIGS. 3 and 5 where it is nominally in parallelism with table top 20. When the pawls 49 of latch members 43 are properly registered in a holding notch as in FIG. 4, the second arm element 50 of latch member 43 is removed from interfering relation with sliding bar or movable stop member 40 so that platform 15 can be rotated from its FIG. 3 position to its FIG. 2 position.

Each of the latch members has a handle 51 attached to it. These handles may be engaged by the user to rotate the latch members in opposition to torsion springs 47 and 48 to spread the latch member away from the table side rails as in FIG. 5 when the footrest assembly is being installed on the x-ray table top.

The footrest assembly may be most easily installed on the side rails by engaging one latch at a time while holding the opposite end of the base or support 27 at an upward inclination relative to table top 20. At the same time a force is applied to manual handle 51 to rock the latch as in FIG. 5. Then, the inclined end of the platform assembly base or support 27 can be let down so its whole length makes contact with the upper surface of table top 20 at which time the latch on the other end is manipulated to spread it away from the side rail after which the assembly may be moved longitudinally as required to effect engagement between the pawls 49 on the latch members and the holding notches in the side rails.

When the footrest assembly is removed from the x-ray table, the platform 15 may be laid down as in FIG. 3 so that the assembly occupies less storage space than would be the case if the platform always had to remain upright in the position in which it is shown in FIG. 2.

On some occasions, the x-ray table shown in FIG. 1 may be tilted in the opposite direction from which it is tilted in FIG. 1 so that the head of the patient would be lower than the feet in which case the footrest platform would have a tendency to rotate back toward its storage position or, in other words, toward parallelism with the x-ray table top. As can be seen best in FIG. 2, inadvertent rotation of the platform 15 is prevented by a detent rod 55 which is surrounded by a spring 56 that is captured between a stationary element 57, which is fixed to the platform and another element 58 which is fixed to the rod and permits loading the spring. The rod is provided with a knob or handle 59 which the user grips to retract detent pin 55 as the platform nearly reaches home position to enable the remote end 60 of the pin 55 to engage in a recess 61 which prevents the platform from rotating.

Although one embodiment of a footrest which is precluded from being rotated to active position unless the footrest assembly is positively latched to the x-ray table has been described in considerable detail, such description is intended to be illustrative rather than limiting, for the invention may be variously embodied and is to be limited only by interpretation of the claims which follow.

We claim:

1. A footrest assembly for an x-ray table top structure which has a longitudinally extending series of spaced apart position holding means at each of its laterally spaced apart sides for enabling said assembly to be engaged with said table top structure at selected longitudinal positions, said footrest assembly comprising:

a support member for extending laterally across said table top, a footrest platform pivotally mounted to said support member for being rotated between attitudes of nominal parallelism and nominal perpendicularity with respect to said table top, movable stop members and means for operatively coupling said stop members to said platform such that when movement of said members is interfered with said platform cannot be rotated out of its nominally parallel attitude, manually operable latch means mounted, respectively, at laterally opposite sides of said support member, each latch means including a first element for releasably engaging with a selected position holding means and a second element which is disposed in non-interfering relationship with respect to said stop member in response to said first element being engaged with a holding means and which is urged into interfering relationship with respect to said stop member in response to said first element not being engaged with a holding means to thereby prevent rotation of said platform from its nominally parallel attitude.

2. The footrest assembly as in claim 1 wherein:

said stop member is an elongated member pivotally connected to said platform on an axis that is offset from the axis about which the platform rotates on the support member such that when the platform is rotated the elongated member is translated, said latch means is comprised of unitary first and second elements and is pivotally mounted on said support means for the second element to be pivoted into a position for interfering with movement of said elongated member when the first element is forced to pivot as a result of it not being engaged by a holding means, and spring means for biasing said latch means in a manner that tends to engage said first element with a holding means.

3. A footrest assembly for being engaged with and disengaged from an x-ray table top structure having means at each of its laterally spaced apart sides providing a series of spaced apart slots for enabling said assembly to be latched in selected longitudinal positions relative to said table top, said footrest assembly comprising:

a support member for extending laterally of said table top, a footrest platform and coaxial pintle shafts fixed to and extending from laterally opposite sides of the platform, laterally spaced apart bearing means on the support member in which said shafts are journaled, respectively, for enabling said platform to be rotated between an attitude of substantial parallelism with the table top and of substantial perpendicularity to it, stop members that are, respectively, pivotally connected to said platform on axes that are offset from the coaxial shaft axes for converting rotational movement of the platform to translational movements of the stop members, spring biased manually turnable latch members pivotally mounted to said support member and each having first and second arm portions joined to each other and extending in different directions from the axis of said pivotal mounting, said first arm portion having pawl means extending therefrom for registering a selected slot at a side of the table top such that when registration has occurred said other arm portion will be pivoted out of interfering relation with said stop member and when registration has not occurred said other arm portion will be in interfering relation with said stop member to thereby prevent rotation of said platform to nominal perpendicularity with said table top.

* * * * *